(12) United States Patent
Chan et al.

(10) Patent No.: US 9,210,938 B2
(45) Date of Patent: Dec. 15, 2015

(54) METHODS FOR MODULATING PHOTOSYNTHETIC ACTIVITY

(71) Applicant: Elwha LLC, Bellevue, WA (US)

(72) Inventors: Alistair K. Chan, Bainbridge Island, WA (US); Roderick A. Hyde, Redmond, WA (US); Jordin T. Kare, Seattle, WA (US); Nathan P. Myhrvold, Medina, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 4 days.

(21) Appl. No.: 13/687,871

(22) Filed: Nov. 28, 2012

(65) Prior Publication Data

US 2014/0148341 A1 May 29, 2014

(51) Int. Cl.
*A01N 37/18* (2006.01)
*A01N 59/02* (2006.01)
*A01G 7/06* (2006.01)

(52) U.S. Cl.
CPC *A01N 59/02* (2013.01); *A01G 7/06* (2013.01); *A01N 37/18* (2013.01)

(58) Field of Classification Search
None
See application file for complete search history.

(56) References Cited

U.S. PATENT DOCUMENTS

| | | | |
|---|---|---|---|
| 7,809,475 B2 * | 10/2010 | Kaprielian | 700/284 |
| 8,182,830 B2 * | 5/2012 | Chen et al. | 424/423 |
| 2007/0075157 A1 | 4/2007 | Lebeda et al. | |
| 2007/0078113 A1 | 4/2007 | Roth et al. | |
| 2008/0171726 A1 | 7/2008 | Roth et al. | |
| 2010/0159135 A1 * | 6/2010 | Bent et al. | 427/255.7 |

FOREIGN PATENT DOCUMENTS

| | | |
|---|---|---|
| CN | 1116044 A | 2/1996 |
| CN | 102210297 A | 10/2011 |

OTHER PUBLICATIONS

Shanxi University; CN 102210297 A—machine translation; <https://www.google.com/patents/CN102210297A?cl=en&dq=cn102210297&hl=en&sa=X&ei=MP1XU4Wsl_PMsQTr5YD4Cw&ved=0CDUQ6AEwAA>, p. 1-3.*
Passel, "Transpiration—Factors Affecting Rates of Transpiration," <http://passel.unl.edu/pages/informationmodule.php?idinformationmodule=1092853841&topicorder=6>, published Mar. 2, 2006, p. 1-3.*
Biotopics, "The light-independent reactions of photosynthesis," <http://biotopics.co.uk/a2/light-independent_reactions.html>, published Apr. 22, 2011, p. 1-3.*
A4F, "Microalgae for food, feed, fuel, and figer—Why this Brief?," <http://algae4feed.org/>, published Jun. 23, 2011, p. 1-3.*
Dawson et al., "Nighttime transpiration in woody plants from contrasting ecosystems," Tree Physiology 27, published Jan. 2, 2007, p. 561-575.*
Kozai et al., "Environmental control for the large-scale production of plants through in vitro techniques," Plant Cell, Tissue, and Organ Culture 51, 1997, p. 49-56.*
García-Mata et al., "Hydrogen sulphide, a novel gasotransmitter involved in guard cell signalling," New Phytologist (2010) 188: 977-984.*
Coyne et al.; "Photosynthesis and Stomatal Light Responses in Snap Beans Exposed to Hydrogen Sulfide and Ozone"; Journal of the Air Pollution Control Association; bearing a date of Nov. 1978; pp. 1119-1123; vol. 28, No. 11; Air Pollution Control Association.
Kim et al.; "Remote Sensing and Control of an Irrigation System Using a Distributed Wireless Sensor Network"; IEEE Transactions on Instrumentation and Measurement; bearing a date of Jul. 2008; pp. 1379-1387; vol. 57, No. 7; IEEE.
PCT International Search Report; International App. No. PCT/US2013/071701; Feb. 27, 2014; pp. 1-4.

* cited by examiner

*Primary Examiner* — Tracy Vivlemore
*Assistant Examiner* — Monica Shin
(74) *Attorney, Agent, or Firm* — Foley & Lardner LLP

(57) ABSTRACT

A method is provided for modulating transpiration in an organism that is capable of photosynthesis, where the method includes contacting the organism with a composition including an effective amount of an oxygen antagonist. Also provided is an apparatus for modulating transpiration in an organism that is capable of photosynthesis.

37 Claims, 2 Drawing Sheets

METHODS FOR MODULATING PHOTOSYNTHETIC ACTIVITY

BACKGROUND

Agriculture requires farmers to obtain sufficient access to water. Water scarcity has become a critical constraint to farming in many parts of the world and shortages of water or drought can adversely affect crop yields. Crop irrigation during periods of low rainfall or drought remains the logical remedy for decreased crop yields and plant death. However, the expense associated with irrigation may be prohibitive and will likely increase as the availability of fresh water declines. Alternatives to irrigation, such as methods that maintain healthy crops during periods of drought, are continuously sought.

Some 2.8 billion people currently live in water-scarce areas. Thus, even in the absence of drought, there is a significant interest in conserving the amount of water that is routinely consumed by plants, including agricultural crops and other plants. For example, a large fully grown tree may evaporate, or "transpire," several hundred gallons of water through its leaves on a hot, dry day. At least ninety percent of the water that enters a plant's roots is used in this process of transpiration.

SUMMARY

According to one exemplary embodiment, the present technology provides a method for modulating transpiration in an organism that is capable of photosynthesis, such as a plant or algae, where the method includes contacting the organism with a composition including an effective amount of an oxygen antagonist. In some embodiments, the oxygen antagonist includes hydrogen sulfide, a prodrug or salt thereof.

According to another exemplary embodiment, the present technology provides an apparatus for modulating transpiration in an organism that is capable of photosynthesis, including: a pump for contacting the organism with a composition including an effective amount of an oxygen antagonist; a sensor; a control unit comprising a microprocessor; a user interface operatively coupled to the control unit; and a communication interface operatively coupled to the control unit.

According to another exemplary embodiment, the present technology provides a method for modulating transpiration in an organism that is capable of photosynthesis, including: contacting the organism with an initial concentration of a composition including an effective amount of an oxygen antagonist; measuring at least one parameter; and increasing or decreasing the initial concentration of the composition that is contacted with the organism; where the parameter is selected from the group consisting of: the amount of light that contacts the organism; the temperature of the organism; the amount of $CO_2$ that is absorbed by the organism; the amount of moisture that is present in the soil surrounding the roots of the organism; and the concentration of the composition within the organism.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The skilled artisan will understand that the drawings primarily are for illustrative purposes and are not intended to limit the scope of the inventive subject matter described herein.

DETAILED DESCRIPTION

The illustrative embodiments described in the detailed description, drawings, and claims are not meant to be limiting. Other embodiments may be utilized, and other changes may be made, without departing from the spirit or scope of the subject matter presented here.

Figure 1:
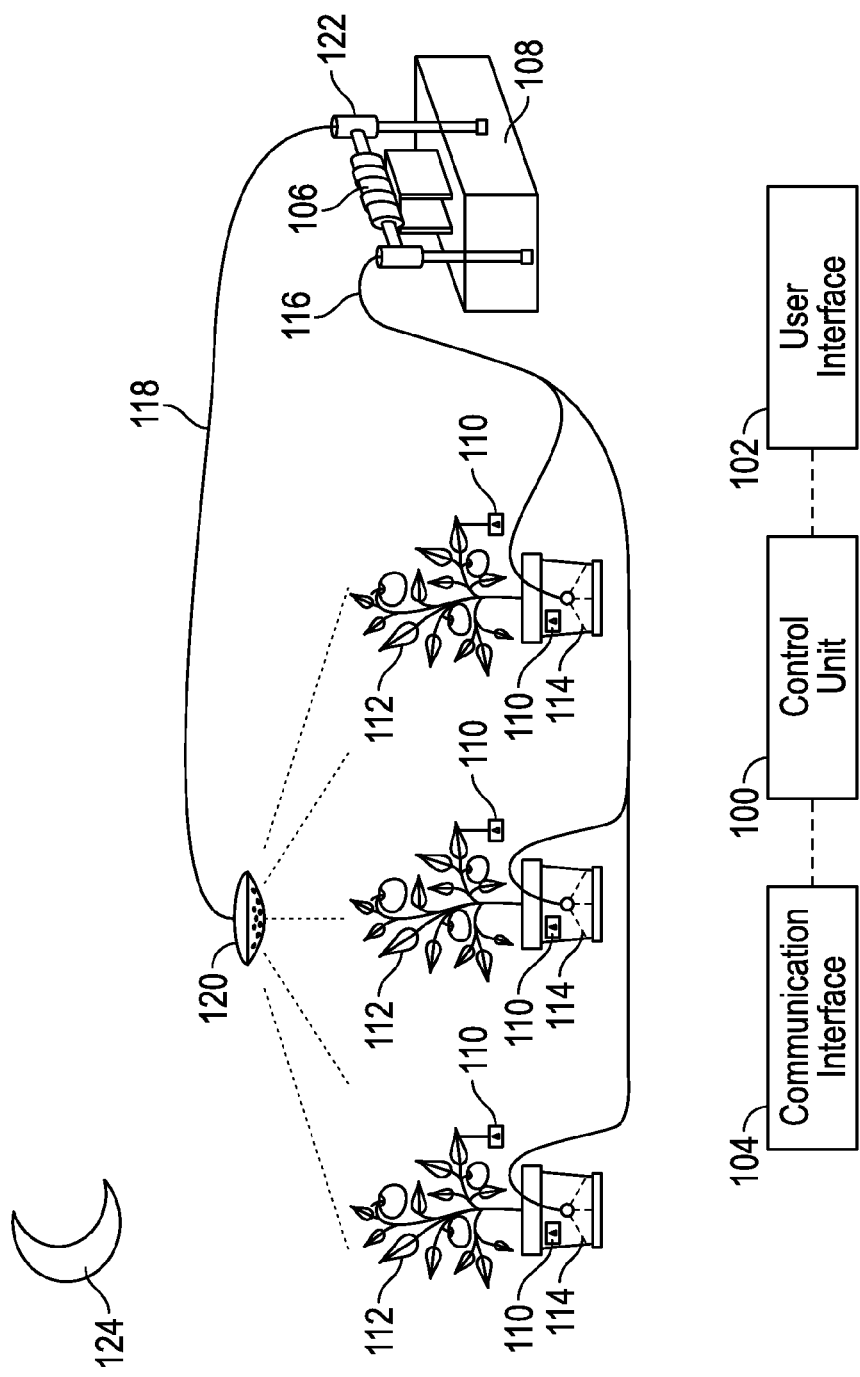
FIG. 1 illustrates, in accordance with one embodiment, a representative apparatus for modulating transpiration in an organism that is capable of photosynthesis.

Referring to FIG. 1, in accordance with one embodiment, illustrations are provided of an apparatus for modulating transpiration in an organism that is capable of photosynthesis, including a pump 106, a sensor 110 such as those shown within the soil or hanging from plants 112, a control unit 100 comprising a microprocessor, a user interface 102 operatively coupled to the control unit, a communication interface 104 operatively coupled to the control unit, where the apparatus is used to contact the organism with a composition comprising an effective amount of an oxygen antagonist. In FIG. 1, receptacle (e.g., container) 108 is provided, for storing a composition that includes the oxygen antagonist. Pump 106 is operatively connected to dispensing lines 116 and 118. In one embodiment, dispensing line 118 delivers the effective amount of an oxygen antagonist to the exterior of plants 112 via spray head 120. In another embodiment, dispensing line 116 delivers the effective amount of an oxygen antagonist to the interior of plants 112 via nozzle 114. In one embodiment, the apparatus is used at night, as represented by moon 124, for modulating transpiration in an organism that is capable of photosynthesis.

Figure 2:
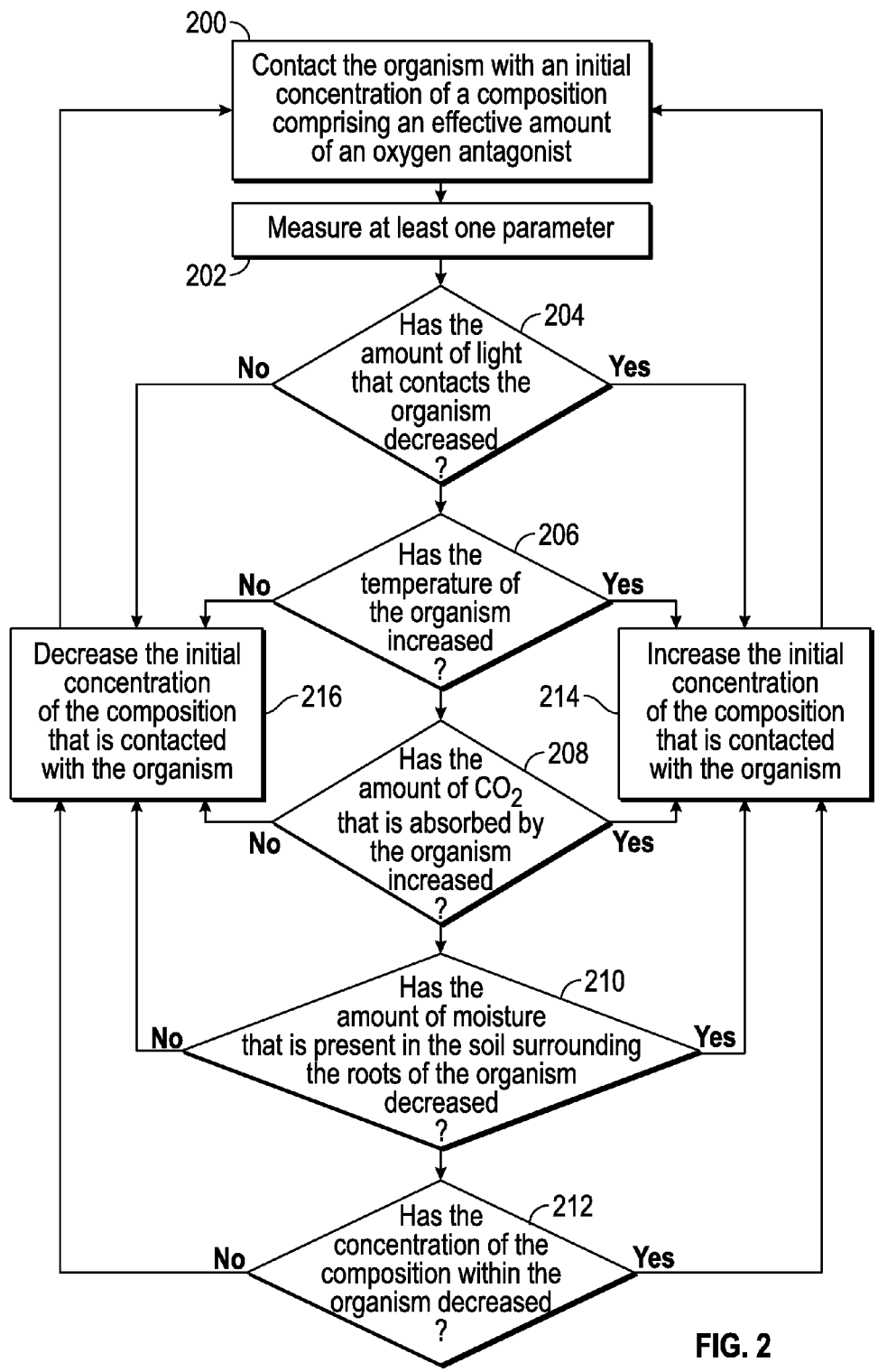
FIG. 2 illustrates a method for method for modulating transpiration in an organism that is capable of photosynthesis, in accordance with one embodiment.

Referring to FIG. 2, a flowchart depicts a method for modulating transpiration in an organism that is capable of photosynthesis, according to one embodiment. The organism is contacted with an initial concentration of a composition comprising an effective amount of an oxygen antagonist (step 200). At least one parameter is measured (step 202), where the parameter is selected from the group consisting of the amount of light that irradiates the organism, the temperature of the organism, the amount of $CO_2$ that is absorbed by the organism, the amount of moisture that is present in the soil surrounding the roots of the organism, and the concentration of the composition within the organism. In some embodiments, if either the amount of light that contacts (i.e., irradiates) the organism has decreased (step 204), the temperature of the organism has increased (step 206), the amount of $CO_2$ that is absorbed by the organism has increased (step 208), the amount of moisture that is present in the soil surrounding the roots of the organism has decreased (step 210), or the concentration of the composition within the organism has decreased (step 212), then the initial concentration of the composition that is contacted with the organism is increased. In other embodiments, if either the amount of light that contacts (i.e., irradiates) the organism has increased (step 204), the temperature of the organism has decreased (step 206), the amount of $CO_2$ that is absorbed by the organism has decreased (step 208), the amount of moisture that is present in the soil surrounding the roots of the organism has increased (step 210), or the concentration of the composition within the organism has increased (step 212), then the initial concentration of the composition that is contacted with the organism is decreased.

The technology is described herein using several definitions, as set forth throughout the specification.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

Heteroalkyl groups include alkyl groups, as defined herein, substituted by one or more O, N, or S atoms.

Aryl groups are cyclic aromatic hydrocarbons that do not contain heteroatoms. Thus aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, and naphthenyl groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups including, but not limited to, amino, alkoxy, alkyl, cyano, and/or halo. In some embodiments, aryl is phenyl or naphthyl. In certain embodiments, aryl is phenyl.

Heteroaryl groups include an aromatic ring containing, for example, 5 to 12, or 5 to 10 atoms including one or more heteroatoms (e.g., 1, 2, 3 or 4 heteroatoms) selected from N, O and S and with the remaining ring atoms being carbon. Heteroaryl groups do not contain adjacent S and O atoms. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. Heteroaryl groups may be monocyclic or polycyclic (e.g., bicyclic, tricyclic). In some embodiments, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine. In some embodiments, more than one ring of a polycyclic heteroaryl group are aromatic. Examples include indole, isoindole, indazole, benzoimidazole, benzotriazole, benzofuran, and benzoxazole.

The terms "alkylene," "heteroalkylene," "arylene," and "heteroarylene," alone or as part of another substituent means a divalent radical derived from an alkyl, heteroalkyl, aryl, or heteroaryl group, respectively, as exemplified by —$CH_2CH_2CH_2CH_2$—. For alkylene, heteroalkylene, arylene, and heteroarylene linking groups, no orientation of the linking group is implied.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —$NH_2$, methylamino, dimethylamino, ethylamino, diethylamino, propylamino, isopropylamino, phenylamino, benzylamino, and the like.

As used herein, the term "transpiration" refers to a process in plants that is similar to evaporation. It is a part of the water cycle in plants, and it is the loss of water vapor from parts of plants (similar to sweating), especially in leaves but also in stems, flowers and roots. Leaf surfaces are dotted with openings which are collectively called stomata, and in most plants they are more numerous on the undersides of the foliage. The stomata are bordered by guard cells that open and close the pore. Leaf transpiration occurs through stomata, and can be thought of as a necessary "cost" associated with the opening of the stomata to allow the diffusion of carbon dioxide gas from the air for photosynthesis.

Plants regulate, in part, the rate of transpiration by the degree of stomatal opening. The rate of transpiration is also influenced by the evaporative demand of the atmosphere surrounding the leaf such as humidity, temperature, wind and incident sunlight. Soil water supply and soil temperature can influence stomatal opening, and thus transpiration rate. The amount of water lost by a plant also depends on its size and the amount of water absorbed at the roots. Stomatic transpiration accounts for most of the water loss by a plant, but some direct evaporation also takes place through the cuticle of the leaves and young stems. Transpiration also cools plants, changes cell's osmotic pressure, and enables mass flow of mineral nutrients and water from roots to shoots. Increases in the following factors may also increase the rate of transpiration: the number of leaves, the number of stomata, light supply, temperature, and water supply. Decreases in the relative humidity will increase the rate of transpiration.

Transpiration rates of plants can be measured according to methods known to those of skill in the art, including the methods described in U.S. Patent Publication No.: 20110270531; "Measurement of Transpiration and Leaf Conductance" Pearcy R W, Schulze E D and Zimmermann R in *Plant Physiological Ecology: Field Methods and Instrumentation* 1989, Eds. R W Pearcy, J Ehleringer, H A Mooney, and P W Rundel, Ch 8, pp 137-160, Chapman and Hall, London; and Groom P, *Elementary Botany,* 1900, G Bell & Sons, London, page 211-214. The transpiration rates of plants can be measured with instruments such as potometers, lysimetes, porometers, photosynthesis systems and heat balance sap flow gauges.

Mass flow of liquid water from the roots to the leaves, i.e., xylem flow, is driven in part by capillary action initiated by transpiration. In taller plants and trees however, the force of gravity can only be overcome by the decrease in hydrostatic (water) pressure in the upper parts of the plants due to the diffusion of water out of stomata into the atmosphere. Water is absorbed at the roots by osmosis, and any dissolved mineral nutrients travel with it through the xylem.

As used herein, the term "stoma" (also stomate; plural stomata) refers to a pore, found in the leaf and stem epidermis that is used for gas exchange. The pore is bordered by a pair of specialized parenchyma cells known as guard cells that are responsible for regulating the size of the opening. The term "stoma" is also used collectively to refer to an entire stomatal complex, both the pore itself and its accompanying guard cells. Air containing carbon dioxide and oxygen enters the plant through these openings where it is absorbed, transported and then used in photosynthesis and respiration, respectively. Oxygen produced by photosynthesis in the spongy layer cells (parenchyma cells with pectin) of the leaf interior exits through these same openings. Also, water vapor is per force released into the atmosphere through these pores via transpiration.

The present technology relates generally to methods for modulating the photosynthetic activity of organism, such a plant or algae, that is capable of photosynthesis where the method includes contacting the organism with a composition including an effective amount of an oxygen antagonist.

In particular, the methods described herein can be used to reduce, for example, the rate of transpiration in plants such as agricultural crops, ornamental plants, and grasses. By reducing the amount of water that is lost by these treated plants, the methods described herein also reduce the amount of water that must be provided (e.g., via irrigation) to such plants.

Without being bound by theory, it is believed the application of a composition that includes an effective amount of an oxygen antagonist to a plant's roots or foliage according to the methods described herein reduces transpiration by decreasing the activity of, or closing, the plant's stoma. Stoma are the minute openings in the epidermis of plants that are regulated by guard cells and through which gases and water vapor are exchanged between the plant's internal spaces and the external atmosphere. Thus, stoma inactivity or closure induced by the application of a composition that includes an effective amount of an oxygen antagonist, according to the methods described herein, may be responsible, at least in part, for the reduction in transpiration, the prevention of drought induced wilting, and the reduction of water use in plants. The present technology can also be used to reduce the volume of water necessary to irrigate the plant and improve the drought-resistance of the plant.

According to one aspect, the present technology provides methods and compositions for reducing the photosynthetic activity of organism, such a plant or algae, that is capable of photosynthesis where the method includes contacting the organism with an effective amount of a composition including an oxygen antagonist. The methods described herein can be used to reduce, for example, the rate of transpiration in plants. Accordingly, the methods described herein can also be used to reduce the amount of water that is lost by algae or plants and, thus, reduce the amount of water that must be provided (e.g., via irrigation) to algae or plants.

The methods described herein are generally intended for use with algae or plants at night, or under conditions where there is an absence of sunlight, such as during cloudy days or when the algae or plants are shaded from light. Without being bound by theory, the methods described herein generally decrease the rate or occurrence of the light-independent (or "dark") reactions during photosynthesis, by which plant enzymes capture $CO_2$ from the atmosphere and release three-carbon sugars, which are later combined to form sucrose and starch. In some embodiments, the methods described herein can generally be used to reduce photosynthetic activity at night, decrease gas exchange, and in so doing, reduce transpiration in plants and the amount of water that is lost by plants through stoma.

Again, without being bound by theory, it is believed that the application of a solution that includes an effective amount of an oxygen antagonist to a plant's roots or foliage according to the methods described herein reduces transpiration by reducing the activity of, or closing, the plant's stoma. As noted above, stoma are the minute openings in the epidermis of plants that are regulated by guard cells and through which gases and water vapor are exchanged from the plant's internal spaces and the external atmosphere. Thus, stoma inactivity or closure induced by the application of a composition that includes an effective amount of an oxygen antagonist according to the methods described herein may be responsible, at least in part, for the reduction in transpiration, the prevention of drought induced wilting, and the reduction of water use in plants. Foliar or root application of compositions that include an effective amount of an oxygen antagonist may result in a reduction of stomatal conductivity, which is indicative of stomatal closure. Reduction of stomatal conductivity results in decreased transpiration and lower water use for the treated plants. In some embodiments, the application of an effective amount of an oxygen antagonist can reduce water use for irrigation by as much as about 10%, 20%, 30%, 40%, 50%, 60%, 70%, 80%, 90%, or a percentage between any two of these values.

Further, reducing transpiration may impact plant physiology in a positive way such as increasing fruit production and/or biomass production. Transpiration reduction may influence the expression of certain genes involved in stress-related functions including disease resistance responses. The treatment of plants according to the methods described herein may also be useful in treating plants prior to transplant to prevent transplant shock and death.

In some embodiments, a method is provided for reducing transpiration or drought-induced wilting in plants such as trees, grasses, and ornamental or agricultural crops. The method includes contacting a plant with a composition including an effective amount of an oxygen antagonist. In one embodiment of the method, a gaseous form, liquid solution, or solid composition of the oxygen antagonist, such as hydrogen sulfide, or a salt or prodrug thereof, is applied to the leaf of the plant or to grass surfaces. In another embodiment of the method, a gaseous form, liquid solution, or solid composition of the oxygen antagonist, such as hydrogen sulfide, or a salt or prodrug thereof, is applied to the base of the plant or the grass for delivery to the plant's root system. In some embodiments, the gaseous form, liquid solution, or solid composition is applied in the evening. For application to the leaf of the plant or grass surfaces, a sufficient application will wet the plant leaves or grass surfaces, for example, by spraying a gas or solution or dusting a solid composition onto the leaf or grass surfaces. For application to the plant's root system, the gas can be delivered by gas lines of (e.g., polyvinylchloride) tubing, or the solution can be delivered, for example, via drip irrigation.

In some embodiments, the contacting step and the amount of the composition including an oxygen antagonist that will be provided to a plant or algae is dependent upon the amount of light that irradiates or contacts the organism. Generally, the composition including an oxygen antagonist will be provided in greater quantities to a plant or algae during periods of darkness and provided in lesser quantities to a plant or algae, or withheld, during the day. For example, the amount of a composition including an oxygen antagonist that is contacted, or the concentration of oxygen antagonist, can be increased as the amount of light that irradiates or contacts the organism decreases. Thus, as the sun gradually sets over a field of crops, the concentration of oxygen antagonist or the volume of composition including an oxygen antagonist that is provided to the crops can be increased. In some embodiments, the contacting occurs based on the time of day, based on a correlation between time and optical irradiation. In some embodiments, the contacting occurs between sunset and sunrise and does not occur between sunrise and sunset. In some embodiments, sunrise and/or sunset are artificially produced by an artificially induced light-dark cycle. For example, an artificially induced light-dark cycle may be attained within a controlled environment from natural light, artificial light, natural darkness, artificially induced darkness, shading, or a combination thereof. The controlled environment may include a greenhouse, grow-house, grow room, or any similar enclosure or partially enclosed structure for growing plants and/or algae that is commonly used by one of skill in the arts of agriculture and/or the cultivation of algae. In some embodiments, the composition inhibits light-independent (i.e., "dark") photosynthetic reactions within the organism.

In some embodiments, the contacting step is dependent upon the temperature of the organism. Generally, the composition including an oxygen antagonist will be increasingly provided to a plant or algae amidst higher temperatures (e.g., above 25° C.) and decreasingly provided to a plant or algae, or withheld, amidst lower temperatures (e.g., below 25° C.). For example, the amount of a composition including an oxygen antagonist that is provided, or the concentration of oxygen antagonist that is provided, can be increased as the air temperature increases. Likewise, the amount of a composition including an oxygen antagonist that is provided, or the concentration of oxygen antagonist that is provided, can be decreased as the air temperature decreases. In some embodiments, the contacting step occurs above a threshold temperature. In some embodiments, the threshold temperature is about 25° C., 30° C., 35° C., 40° C., 45° C., 50° C., or a temperature between any two of these temperatures.

In some embodiments, the contacting step is dependent upon the amount of $CO_2$ that is absorbed by the organism. Generally, the composition including an oxygen antagonist will be increasingly provided to a plant or algae to reduce the rate of absorption of atmospheric $CO_2$ by the organism. As such, the composition including an oxygen antagonist can be increasingly provided during periods (e.g., at night) when atmospheric $CO_2$ is actively absorbed by the organism, and decreasingly provided during periods (e.g., during the day) when atmospheric $CO_2$ is less actively absorbed by the organism. In some embodiments, the method of providing an effective amount of a composition including an oxygen antagonist to the organism further includes reducing the rate of absorption of atmospheric $CO_2$ by the organism.

In some embodiments, the contacting step is dependent upon the amount of moisture that is present in the soil surrounding the roots of the organism. Generally, the composition including an oxygen antagonist will be provided to a plant or algae to reduce the amount of water that must be administered to the plant or algae. As such, the composition including an oxygen antagonist can be increasingly provided during hot and/or dry periods, and decreasingly provided during cool and/or wet periods. In some embodiments, the method of providing an effective amount of a composition including an oxygen antagonist to the organism further includes measuring the amount of moisture that is present in the soil surrounding the roots of the organism.

The term "effective amount" means an amount that can achieve the stated result. As used herein, an "effective amount" is, for example, an amount that reduces the rate of photosynthesis in an organism that is capable of photosynthesis, or an amount that reduces the rate of transpiration in a plant. As used herein, an effective amount is one that reduces transpiration in a plant as determined, for example, from transpiration rates as measured according to methods known to those of skill in the art, including the methods described in Pearcy R W, et al., supra.

As used herein, the term "oxygen antagonist" refers to a substance that competes with oxygen as it used by an organism capable of photosynthesis. An oxygen antagonist effectively reduces or eliminates the amount of oxygen that is available to the organism, for instance, by binding sites on cytochrome c oxidase that would otherwise bind to oxygen. Cytochrome c specifically binds oxygen and then converts it to water. In some embodiments, such binding to cytochrome c oxidase is preferably releasable and reversible binding. In some embodiments, an oxygen antagonist is evaluated by measuring ATP and/or carbon dioxide output. Non-limiting examples of oxygen antagonists include hydrogen sulfide ($H_2S$) and carbon monoxide (CO).

As used herein, the term "hydrogen sulfide" refers to $H_2S$. In some embodiments, the hydrogen sulfide is a salt or prodrug of hydrogen sulfide.

Hydrogen sulfide is a highly toxic gas that is denser than air. Due to its extreme toxicity, hydrogen sulfide will generally be provided to the organism capable of photosynthesis at a low concentration that is neither toxic to the organism nor to humans. Alternatively, hydrogen sulfide will generally be provided to the organism capable of photosynthesis within an enclosed structure, such as a greenhouse, from which people are excluded.

Typical levels of hydrogen sulfide contemplated for use in accordance with the present methods include values that are not harmful or toxic to humans that are in the vicinity of the methods of use described herein. The concentration of the hydrogen sulfide in the compositions of the methods described herein can and will vary. In this regard, the compositions including hydrogen sulfide may include about $10^{-7}$ ppm hydrogen sulfide, $10^{-6}$ ppm hydrogen sulfide, $10^{-5}$ ppm hydrogen sulfide, $10^{-4}$ ppm hydrogen sulfide, $10^{-3}$ ppm hydrogen sulfide, 0.01 ppm hydrogen sulfide, 0.1 ppm hydrogen sulfide, 1.0 ppm hydrogen sulfide, 10.0 ppm hydrogen sulfide, 100.0 ppm hydrogen sulfide, $10^3$ ppm hydrogen sulfide, or a range between and including any two of these values. The methods described herein may be carried out in a variety of ways, such as by contacting the organism with a composition including an oxygen antagonist, such as hydrogen sulfide, whether in solid, liquid, or gaseous form. As used herein, "contacting" means to bring the composition including an oxygen antagonist and an organism into intimate association with each other.

Hydrogen sulfide, $H_2S$, can be generated in several ways. One way is to bubble hydrogen sulfide gas into a liquid medium or carrier (such as water) until saturation. In some embodiments, the carrier solution (such as water) is saturated with gaseous $H_2S$ and diluted roughly 10-fold to 100-fold. After this dilution, the $H_2S$ of the final solution should range from about $10^{-7}$ wt. % to about 5 wt. %. Alternatively, hydrogen sulfide may be prepared in situ from a salt of hydrogen sulfide or from a hydrogen sulfide prodrug, precursor compound or polymer, as described herein.

Hydrogen sulfide, $H_2S$, can be generated from salts of hydrogen sulfide. Salts of hydrogen sulfide include sodium sulfide ($Na_2S$), sodium hydrosulfide (NaHS), potassium sulfide ($K_2S$), potassium hydrosulfide (KHS), or a mixture thereof. Such salts may be dissolved in a liquid carrier. For example, these salts will dissolve in water readily, and $H_2S$ is generated in situ. At a pH of 7.4, for example, about 30% of sulfide whether derived from gaseous $H_2S$ or one of its alkali salts will exist in the form of $H_2S$, with the anion $HS^-$ consisting of the balance. NaHS dissociates to form $Na^+$ and $HS^-$ in solution, and then $HS^-$ combines with $H^+$ to form $H_2S$. As such, the hydrogen sulfide can be added to the liquid carrier as a dissolved salt, such as $Na_2S$, NaHS, $K_2S$, KHS, or a mixture thereof, where the solution has a concentration of hydrogen sulfide that ranges from about $10^{-7}$ wt. % to about 5 wt. % of the dissolved salt in the liquid carrier.

Hydrogen sulfide, $H_2S$, can be generated from prodrugs i.e., precursors of hydrogen sulfide, such as hydrogen sulfide releasing compounds or hydrogen sulfide releasing polymers. Prodrugs or precursors of hydrogen sulfide include any hydrogen sulfide releasing molecule or hydrogen sulfide releasing polymer (e.g., containing thioamide or thiourea groups) such as those disclosed in U.S. Pat. No. 7,879,827, titled Derivatives of 4- or 5-Aminosalicylic acid to Wallace et al., U.S. Pat. No. 8,182,830, titled Hydrogen Sulfide Generating Polymers to Chen et al., and the published US Patent Application No. 2010/0159135, titled Process for In Situ Generation of Hydrogen Sulfide Gas From a Solid Precursor to Bent et al. Hydrogen sulfide releasing compounds or polymers, such as those that include thioamide or thiourea groups, may be hydrolyzed to release hydrogen sulfide in situ. As such, the hydrogen sulfide precursor compound or polymer can be added to the liquid carrier, or added in solid form directly to the organism capable of photosynthesis or surrounding soil, to generate $H_2S$ in situ and provide a concentration of hydrogen sulfide that ranges from about $10^{-7}$ wt. % to about 5 wt. % in the liquid carrier or directly into or in the vicinity of the organism capable of photosynthesis. For example, the hydrogen sulfide precursor compound or polymer can be added to the soil surrounding a crop to gradually deliver $H_2S$ to the roots of the crop.

Scheme 1

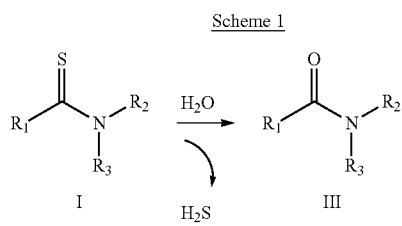

Representative hydrogen sulfide releasing compounds include those of Formula I, where $R_1$ is selected from hydrogen, amino, alkyl, heteroalkyl, aryl, and heteroaryl; and each $R_2$ and $R_3$ is independently selected from hydrogen, alkyl, and aryl. Representative hydrogen sulfide releasing compounds include thioacetamide and thiourea.

Scheme 2

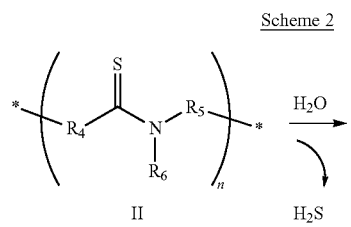

-continued

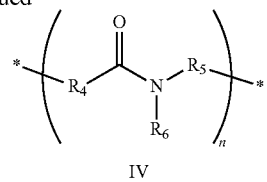

Representative hydrogen sulfide releasing polymers include those of Formula II, where $R_4$ is selected from amino, alkylene, heteroalkylene, arylene, and heteroarylene; and $R_5$ is selected from alkylene, and arylene; $R_6$ is selected from hydrogen, alkyl, and aryl; and n is from 1 to 1,000. In another embodiment, the hydrogen sulfide releasing polymer is copolymerized with polycarbonate, polyolefin, polyamide, polyester, polyacrylate, or a mixture thereof. In another embodiment, the polyacrylate includes monomer units selected from the group consisting of methyl methacrylate, butyl methacrylate, hexyl methacrylate, ethyl methacrylate, 2-ethoxyethyl methacrylate, methyl acrylate, ethyl acrylate, hexyl acrylate and butyl acrylate.

In some embodiments, the compositions described herein include one or more excipients such as a solid or liquid carrier, an adhesive agent, fungicide, antibiotic, pesticide, antiviral agent, anti-herbivore agent, plant nutrient, fertilizer, growth regulator, particulate material, surfactant, dispersant, wetting agent, filler, inert additive, or a combination thereof. Some of such excipients commonly used in the art can be found in the John W. McCutcheon, Inc. publication Detergents and Emulsifiers, Annual, Allured Publishing Company, Ridgewood, N.J., U.S.A.

In some embodiments, the formulation includes an aqueous carrier, i.e., the composition further includes water. The quantity of water may be suitable for the preparation of directly sprayable solutions. In some embodiments, the compositions described herein comprise an aqueous medium. In some embodiments, the composition includes an aqueous carrier. Non-limiting examples of an aqueous medium include an aqueous liquid (e.g., fluid or solution), aqueous gel, or aqueous suspension. In some embodiments, the composition is an aqueous liquid. In some embodiments, the composition is an aqueous gel. In some embodiments, the composition is an aqueous suspension. The amount of aqueous medium in the composition can be from about 0.1 wt. % to about 5 wt. %, from about 5 wt. %, to about 10 wt. %, from about 10 wt. %, to about 25 wt. %, from about 25 wt. %, to about 50 wt. %, from about 50 wt. %, to about 75 wt. %, from about 75 wt. %, to about 99 wt. %, or a range between and including any two of these values.

Non-aqueous carriers (i.e., organic liquids/solvents) suitable for this purpose include those described herein, e.g., as organic liquids, such as aromatic solvents (e.g., xylene), paraffins (e.g., mineral oil fractions), alcohols (e.g., methanol, butanol, pentanol, benzyl alcohol), ketones (e.g., cyclohexanone, methyl hydroxybutyl ketone, diacetone alcohol, mesityl oxide, isophorone), lactones (e.g., gamma-butyrolactone), pyrrolidones (e.g., pyrrolidone, N-methylpyrrolidone, N-ethylpyrrolidone, n-octylpyrrolidone), acetates (glycol diacetate), glycols, dimethyl fatty acid amides, fatty acids and fatty acid esters. In principle, solvent mixtures may also be used. The amount of non-aqueous medium in the composition can be from about 0.1 wt. % to about 5 wt. %, from about 5 wt. %, to about 10 wt. %, from about 10 wt. %, to about 25 wt. %, from about 25 wt. %, to about 50 wt. %, from about 50 wt. %, to about 75 wt. %, from about 75 wt. %, to about 99 wt. %, or a range between and including any two of these values.

In some embodiments, particulate materials or particulate carriers, including hydrophilic particles, are used to help the composition adhere to the plant. Non limiting particulate materials include, for example, chaff, calcined calcium carbonate, calcined talc, calcined kaolin, baked kaolin, fired kaolin, metakaolin, calcined bentonites, calcined clays, calcined pyrophyllite, $SiO_2$, calcined silica, calcined feldspar, calcined sand, calcined quartz, calcined chalk, calcined limestone, calcined precipitated calcium carbonate, baked calcium carbonate, calcined diatomaceous earth, calcined barytes, calcined aluminum trihydrate, calcined pyrogenic silica, calcined titanium dioxide dehydrated kaolin, dehydrated calcium carbonate, dehydrated bentonites, dehydrated limestone, plastic, and combinations thereof. The amount of particulate materials in the composition can be from about 0.1 wt. % to about 5 wt. %, from about 5 wt. %, to about 10 wt. %, from about 10 wt. %, to about 25 wt. %, from about 25 wt. % to about 50 wt. %, or a range between and including any two of these values.

As used herein, the terms "filler" and "inert additive" refer to any standard filler or inert additive that is commonly used in agricultural formulations. Examples of such fillers and inert additives further include, but are not limited to, any of the particulate materials or particulate carriers described above. The amount of filler and/or inert additive in the composition can be from about 0.1 wt. % to about 5 wt. %, from about 5 wt. %, to about 10 wt. %, from about 10 wt. %, to about 25 wt. %, from about 25 wt. % to about 50 wt. %, from about 50 wt. %, to about 75 wt. %, from about 75 wt. %, to about 99 wt. %, or a range between and including any two of these values.

As used herein, the term "adhesive agent" refers to a liquid or solid material that improves the adhesion of the compositions described herein to a plant. Adhesive agents can aid in spraying uniform treatments on a plant or horticultural substrate. Non-limiting adhesive agents include, for example, modified phthalic glycerol alkyd resins such as Latron B-1956 from Rohm & Haas Co.; plant oil based materials (cocodithalymide) with emulsifiers; polymeric terpenes; nonionic detergents (ethoxylated tall oil fatty acids); guar gum; xanthane gum, latex, agar, starch, epoxide derivatives (e.g., EP30HT® sold by Masterbond, Inc., Hackensack, N.J.), non-petroleum based adhesive resins, biodegradable resins, milk-based glues, and the like. The adhesive agent is generally non-toxic and may have high optical clarity and temperature resistance.

Exemplary non-limiting fungicides include, but are not limited to, copper chelate, which is used to treat ash yellows, Dutch elm disease and fruit tree-related fungus problems; mefenoxam ((R)-2[(2,6-dimethylphenyl)-metho-xyacetylamino]-propionic acid methyl ester), which is used to treat certain plant diseases in nonbearing citrus, nonbearing deciduous fruits and nuts, ornamentals, and shade trees; propiconazole, which is used to treat broad spectrum systemic disease control; and others. The amount of adhesive agent in the composition can be from about 0.1 wt. % to about 5 wt. %, from about 5 wt. %, to about 10 wt. %, from about 10 wt. %, to about 25 wt. %, from about 25 wt. % to about 50 wt. %, or a range between and including any two of these values.

Exemplary non-limiting antibiotics include, but are not limited to oxytetracycline and streptomycin. The amount of antibiotics in the composition can be from about 0.001 wt. % to about 0.01 wt. %, from about 0.01 wt. %, to about 0.1 wt. %, from about 0.1 wt. %, to about 1 wt. %, from about 1 wt. %, to about 10 wt. %, or a range between and including any two of these values.

Exemplary non-limiting pesticides include, but are not limited to, abamectin B1, which is used for insect pest control for woody trees and shrubs for beetles, lace bugs, spider mites and leaf miners; imidacloprid, which is used for broad spectrum control for adelgid, armored scales, Asian longhorned beetle, aphids, elm leaf beetles, black vine weevil larvae, eucalyptus longhorned borer, flatheaded borers (including bronze birch borer and alder-birch borer), Japanese beetles, lace bugs, leaf hoppers, leaf miners, mealy bugs, sawfly larvae, pine tip moth larvae, psyllids, royal palm bugs, scale insects, thrips (suppression) and whiteflies; azadirachtin, which is used for insect pest control for aphids, armyworms, bagworms, beetles, grubs and weevils, cankerworms, caterpillars, loopers and moths, chafers, cutworms, flies, greenhouse leaf tiers, leaf hoppers, leaf miners, leaf rollers, leaf perforators, marsh crane flies, mealy bugs, psyllids, sawflies, thrips and whiteflies; nicotine sulfate, which is used for control of mites. The amount of pesticides in the composition can be from about 0.001 wt. % to about 0.01 wt. %, from about 0.01 wt. %, to about 0.1 wt. %, from about 0.1 wt. %, to about 1 wt. %, from about 1 wt. %, to about 10 wt. %, or a range between and including any two of these values.

Non-limiting plant nutrients include, for example, nitrogen, magnesium, calcium, boron, potassium, copper, iron, phosphorus, manganese, zinc, and salts thereof. The amount of nutrients in the composition can be from about 0.001 wt. % to about 0.01 wt. %, from about 0.01 wt. %, to about 0.1 wt. %, from about 0.1 wt. %, to about 1 wt. %, from about 1 wt. %, to about 10 wt. %, or a range between and including any two of these values.

In some embodiments, the compositions include surfactants, dispersants, and combinations thereof. The amount of surfactants and/or dispersants in the composition can be from about 0.1 wt. % to about 5 wt. %, from about 5 wt. %, to about 10 wt. %, from about 10 wt. %, to about 25 wt. %, from about 25 wt. % to about 50 wt. %, or a range between and including any two of these values. Surfactants and dispersants include nonionic surfactants, anionic surfactants, cationic surfactants and/or amphoteric surfactants. Surfactants and dispersants can improve the quality of slurry compositions and help particulate materials to remain in solution during spraying. Surfactants and dispersants also function to break-up agglomerates of particulate materials.

Suitable surfactants include alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ether, tributylphenyl polyglycol ether, tristerylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable dispersants include lignosulfite waste liquors and methylcellulose.

In some embodiments, the compositions include wetting agents. The amount of surfactants and/or dispersants in the composition can be from about 0.1 wt. % to about 5 wt. %, from about 5 wt. %, to about 10 wt. %, from about 10 wt. %, to about 25 wt. %, from about 25 wt. % to about 50 wt. %, or a range between and including any two of these values. Wetting agents reduce surface tension of water in the slurry and thus increase the surface area over which a given amount of the slurry may be applied. Non limiting wetting agents include, for example, fatty acids and silanes. Fatty acids include fatty acids such as Hystreneo® or Industrene® products obtained from Witco Corporation or Emersol® products, including the stearic acid and stearate salts, obtained from Henkel Corporation. Silanes include the organofunctional silanes such as Silquest® products obtained from Witco or modified silicone fluids such as the DM-Fluids® obtained from Shin Etsu.

Solid, liquid, and gaseous compositions including an oxygen antagonist, such as hydrogen sulfide, or a salt or prodrug of hydrogen sulfide, can be prepared by various conventional procedures. Thus, the active ingredient (i.e., the oxygen antagonist or a salt or prodrug thereof), may be applied in gaseous form, dissolved in a liquid solution, or tumbled together with a finely divided solid carrier. Alternatively, the active ingredient in liquid form, including mixtures, solutions, dispersions, emulsions and suspensions thereof, may be admixed with a solid carrier in finely divided form. Furthermore, the oxygen antagonist or a salt or prodrug thereof in solid form may be admixed with a liquid carrier to form a mixture, solution, dispersion, emulsion, suspension or the like.

In some embodiments, the composition including an oxygen antagonist is a gas consisting essentially of the oxygen antagonist. In still further embodiments, the composition including an oxygen antagonist, such as hydrogen sulfide, may form a mixture with one or more other gases. In some cases, it is contemplated that the other gas is a nonreactive gas such as nitrogen ($N_2$). In some embodiments, the composition including an oxygen antagonist is a gas that includes one or more other gases and that includes about $10^{-7}$ wt. % to about 5 wt. % hydrogen sulfide.

In one embodiment of the method, a gaseous form of the oxygen antagonist, such as hydrogen sulfide, or a salt or prodrug thereof, is applied to the leaf of the plant or to grass surfaces. In another embodiment of the method, a gaseous form of the oxygen antagonist, such as hydrogen sulfide, or a salt or prodrug thereof, is applied to the base of the plant or the grass for delivery to the plant's root system. In some embodiments, the gaseous form is applied in the evening. The amount and frequency of the application of the gas to the plant to effect a reduction in transpiration and prevention of wilting may vary depending upon the plant's environment.

In other embodiments, the composition including an oxygen antagonist is a solid. In some embodiments, the solid composition including an oxygen antagonist is a solid that includes about $10^{-7}$ wt. % to about 5 wt. % hydrogen sulfide, or a salt or prodrug of hydrogen sulfide. In one embodiment of the method, a solid composition of the oxygen antagonist, such as hydrogen sulfide, or a salt or prodrug thereof, is applied to the leaf of the plant or to grass surfaces. In another embodiment of the method, a solid composition of the oxygen antagonist, such as hydrogen sulfide, or a salt or prodrug thereof, is applied to the base of the plant or the grass for delivery to the plant's root system. In some embodiments, the solid composition is applied in the evening. The amount and frequency of the application of the solid composition to the plant to effect a reduction in transpiration and prevention of wilting may vary depending upon the plant's environment.

In other embodiments, the composition including an oxygen antagonist is a liquid. In some embodiments, the liquid composition including an oxygen antagonist is a liquid that includes about $10^{-7}$ wt. % to about 5 wt. % hydrogen sulfide, or a salt or prodrug of hydrogen sulfide. In another embodiment of the method, a liquid solution of the oxygen antagonist, such as hydrogen sulfide, or a salt or prodrug thereof, is applied to the base of the plant or the grass for delivery to the plant's root system. In some embodiments, the solution is applied in the evening. For application to the leaf of the plant or grass surfaces, a sufficient application will wet the plant leaves or grass surfaces by, for example, by spraying the solution onto the leaf or grass surfaces. For application to the plant's root system, the solution can be delivered, for example, via drip irrigation. The amount and frequency of the application of the solution to the plant to effect a reduction in transpiration and prevention of wilting may vary depending upon the plant's environment.

Liquid forms, as used herein, include solutions, dispersed forms, coatings, or sprays, as discussed herein. In some embodiments, the composition is a coating. In other embodiments, the coating is a spray-on coating. One method of spraying is using an atomizer such as, for example, a DeVilbiss atomizer. The composition of the present methods, having an oxygen antagonist or a salt or prodrug thereof, can also be applied as aerosols, e.g., by dispersing them in air using a compressed gas such as, for example, nitrogen, carbon dioxide, dichlorodifluoromethane, trichlorofluoromethane, or other halocarbons.

In some embodiments, the composition of the present methods is an emulsion, paste or oil dispersion that includes water and/or one or more organic liquids such as methanol, ethanol, propanol, iso-propanol, iso-butanol, acetone, methyl ethyl ketone, ethylene oxide, propylene oxide, tetrahydrofuran, or combinations thereof. In some embodiments, the composition includes a liquid carrier. Organic liquids can be added to the compositions described herein to form a slurry and this slurry can optionally be diluted with water to form an aqueous dispersion. The resulting slurry can retain the particulates of the compositions described herein in finely divided form. Typically, the organic liquids are used in an amount sufficient to form a dispersion of the compositions described herein. The amount of water and/or organic liquid in the composition can be from about 0.1 wt. % to about 5 wt. %, from about 5 wt. %, to about 10 wt. %, from about 10 wt. %, to about 25 wt. %, from about 25 wt. %, to about 50 wt. %, or a range between and including any two of these values.

The composition of the present methods, having an oxygen antagonist or a salt or prodrug thereof, can be encapsulated into a molecular encapsulation agent. Encapsulating agents include, for example, cyclodextrins, crown ethers, polysiloxanes, and zeolites. In some embodiments, encapsulating agents include, for example, one or more of α-cyclodextrin, β-cyclodextrin, and γ-cyclodextrin. The encapsulating agent can and will vary. As one skilled in the art will appreciate, any cyclodextrin or mixture of cyclodextrins, cyclodextrin polymers as well as modified cyclodextrins can also be utilized. Cyclodextrins are available from Wacker Biochem Inc., Adrian, Mich. or Cerestar USA, Hammond, Ind., as well as other vendors.

As noted, the present technology relates generally to methods and compositions for modulating the photosynthetic activity of organism, such a plant or algae, that is capable of photosynthesis where the method includes contacting the organism, such as a plant or algae, with a composition including an effective amount of an oxygen antagonist. In some embodiments, the contacting includes providing the oxygen antagonist to the leaves or roots of the plant. In some embodiments, the composition is provided into the vasculature system of the plant or to the immediate proximity thereof. In some embodiments, the composition is provided into the phloem or xylem of the tree or to the immediate proximity thereof. In some embodiments, the method further includes monitoring the amount of water removed from soil by the plant.

The organism capable of photosynthesis will generally be contacted in the evening, after sunset, with the oxygen antagonist. The amount of time the organism capable of photosynthesis is contacted to the oxygen antagonist can and will vary. In some embodiments, the organism is contacted with the oxygen antagonist for about, for at least about, or for at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more minutes and/or, 1, 2, 3, 4, 5, 6, 7, 8, 9, 10, 11, 12 or more hours.

In some embodiments, the organism capable of photosynthesis may be contacted to the oxygen antagonist in an enclosed structure such as a greenhouse or a shroud. In some cases, the greenhouse can maintain particular environment or modulate the environment as is desired. The environment refers to the amount of oxygen antagonist with which the organism capable of photosynthesis is exposed and/or the temperature of the environment. Thus, the methods described herein can include a step of subjecting the organism capable of photosynthesis, within a greenhouse, to a controlled temperature environment. In some cases, the organism capable of photosynthesis is placed under a vacuum before, during, or after exposure to an oxygen antagonist. In other cases, the biological matter is exposed to a nontoxic environment after being exposed to an oxygen antagonist.

Moreover, in other embodiments, the greenhouse containing the organism capable of photosynthesis cycles at least once to a different amount or concentration of the oxygen antagonist, where the difference in amount or concentration is by at least one percentage difference. The greenhouse may cycle back and forth between one or more amounts or concentrations of the oxygen antagonist, or it may gradually increase or decrease the amount or concentrations of an oxygen antagonist. In some cases, the different amount or concentration is between about 0 and 99.9% of the amount or concentration of the oxygen antagonist to which the organism capable of photosynthesis was initially exposed. It is contemplated that the difference in amount and/or concentration is about, at least about, or at most about 0.1, 1, 10, 25, 50, 75, 99%, or any range derivable therein.

As used herein, the term "organism capable of photosynthesis" includes any plant or microorganism (e.g., bacterium or algae) having chloroplasts for photosynthetic reactions.

In some embodiments, the organism is a plant. As used herein, the term "plant" refers to any green plant having chloroplasts for photosynthetic reactions. In some embodiments, the plant includes fruiting, agricultural, and ornamental crops and the products thereof, including those selected from the group consisting of fruits, vegetables, trees, shrubs, flowers, grasses, roots, seeds, landscape plants, ornamental plants, and agricultural plants. In some embodiments, the plant is grown on a farm, orchard, or in a forest. In some embodiments, the plant is a tree. In some embodiments, the plant is grown in a controlled environment, such as a greenhouse, grow-house, grow room, or any similar enclosure, or partially enclosed structure, for growing plants and/or algae that is commonly used by one of skill in the arts of agriculture and/or the cultivation of algae. In some embodiments, the controlled environment includes a natural light-dark cycle. In some embodiments, the controlled environment includes an artificial light-dark cycle. The artificial light-dark cycle may include natural light, artificial light, natural darkness, artificially induced darkness, shading, or a combination thereof.

The algae described herein may be collected and processed into a feedstuff (i.e., any edible substance that is ingestible by any animal such as grains, fruits, vegetables, leaves, grasses etc.) or feedstock (i.e., any chemical or polymer feedstock used for industrial purposes such as hydrocarbons, sugars, alcohols, peptides, proteins, natural rubber, synthetics, bioethanol, biodiesel, biomass, etc.)

The plants described herein include agricultural plants of which a part or all is harvested or cultivated on a commercial scale or which serve as an important source of a feedstuff or feedstock as described above, fibers (e.g., cotton, linen), combustibles (e.g., wood) or other chemical compounds. Agricultural plants also encompass horticultural plants, i.e., plants grown in gardens (and not on fields), such as certain fruits and vegetables. Examples of agricultural plants include soybean, corn (maize), wheat, triticale, barley, oats, rye, rape, such as canola/oilseed rape, millet (sorghum), rice, sunflower, cotton, sugar beets, pome fruit, stone fruit, citrus, bananas, strawberries, blueberries, almonds, grapes, mango, papaya, peanuts, potatoes, tomatoes, peppers, cucurbits, cucumbers, melons, watermelons, garlic, onions, carrots, cabbage, beans, peas, lentils, alfalfa (lucerne), trefoil, clovers, flax, herbs, grasses, including but not limited to elephant grass (Miscanthus), lettuce, sugar cane, tea, tobacco and coffee. Agricultural plants further include floricultural plants such as flowering plants, household plants, ornamental plants, or any such adornment-producing plant.

Plants treated with the compounds and by the methods of the present invention are preferably treated with a non-phytotoxic amount of an oxygen antagonist or a salt or prodrug thereof.

The amount of the composition to be applied can and will vary depending upon a number of factors including the manner of application, the identity of the plant, the amount of plants per hectare and the concentration of the composition. The quantity of composition applied may be from about 0.1 kg per hectare to about 1 kg per hectare, from about 1 kg per hectare to about 10 kg per hectare, from about 10 kg per hectare to about 100 kg per hectare, or a range between and including any two of these values. In some embodiments, the composition is coated with an application-density of at least about 1 kg per hectare.

In some embodiments, the plant's rate of transpiration is intended to be decreased by about 5% to about 10%, about 10% to about 20%, about 20% to about 30%, about 30% to about 40%, about 40% to about 60%, about 60% to about 80%, about 80% to at least about 100%, or a range between and including any two of these values, after the initial contacting step, during a period of time of from about one day to about one week, from about one week to about one month, from about six months to about one year, from about one year to about five years, or a range between and including any two of these values.

In some embodiments, the amount of water consumed by the plant is intended to be reduced by about 5% to about 10%, about 10% to about 20%, about 20% to about 30%, about 30% to about 40%, about 40% to about 60%, about 60% to about 80%, or a range between and including any two of these values, after the initial contacting step, during a period of time of from about one day to about one week, from about one week to about one month, from about six months to about one year, from about one year to about five years, or a range between and including any two of these values.

In some embodiments, the method is at least partially automated. In some embodiments, the method further includes: taking a first measurement of the amount of water removed from soil by the plant over a period of time; providing the plant with an amount of a composition including an oxygen antagonist; and taking a second measurement of the amount of water removed from soil by the plant over a period of time, where the second measurement is reduced relative to the first measurement.

According to another exemplary embodiment, the present technology provides an apparatus for modulating transpiration in an organism that is capable of photosynthesis, including:

i. a pump for contacting an organism with a composition including an effective amount of an oxygen antagonist;
ii. a sensor;
iii. a control unit including a microprocessor;
iv. a user interface operatively coupled to the control unit; and
v. a communication interface operatively coupled to the control unit.

The Pump (i): Suitable pumps are well known in the art and in industries such as the oil industry (e.g., for the injection or extraction of subsea gasses or fluids or the healthcare industry (e.g., for the infusion of fluids into a patient). See, e.g., U.S. Pat. No. 6,270,478 entitled Infusion Pump System and an Infusion Pump Unit to Mernoe et al.; U.S. Pat. No. 6,213,738 entitled Volumetric Infusion Pump to Danby et al.; and U.S. Pat. No. 5,743,878 Infusion Pump to Ross et al. Such pumps can be simple pumps which are either "on" or "off," or may comprise a programmable controller (referred to in the art as a "smart pump") that may be integral to the pump or exist as a separate controller unit interfaced in a wired (e.g., via hard wiring, a serial port, a USB port, a "fire wire" port, etc.) or wireless fashion (e.g., connected an via infrared connection, a radio frequency connection, a "bluetooth" connection, etc.). Each of the pumps may communicate with components (ii)-(v). In one embodiment each of the pumps may include technology (e.g., bluetooth) for wireless communication. Where additional information is available from components (ii)-(v) it is contemplated that the control unit of the pumps may be programmed or otherwise configured to collect the information and use the information to modify pump rates.

The Sensors (ii): One or more sensors may be used to obtain and monitor data related to the one or more organisms. Each sensor is independently located in the vicinity of an organism, within an organism, or on the surface of an organism. Each sensor can be used to obtain and monitor data, for example, related to the concentration of $H_2O$, $CO_2$, or concentrations or delivery rates of the composition including an effective amount of an oxygen antagonist. Each sensor can also be used to obtain and monitor data, for example, related to atmospheric temperature, organism temperature, time of day, date, humidity, organism moisture level, wind speed, sunlight level, the amount of water provided to the organism, the amount of moisture in the soil surrounding the organism, the transpiration rate of the organism, guard cell morphology (e.g., expansion or contraction), or the rate of injection of the composition including an effective amount of an oxygen antagonist into the organism. The sensors obtain and monitor such data related to the organism and provide the data to the control unit including a microprocessor.

The Control Unit and User Interface (iii)-(iv): The control unit including a microprocessor receives data related to one or more organisms from the sensors, as described above, to coordinate and optimize the administration of the composition including an effective amount of an oxygen antagonist into the organism. For example, the control unit can set initial irrigation rates or rates at which the composition including an effective amount of an oxygen antagonist is provided to the organism. After receiving data from the sensors, the control unit can adjust and optimize such initial rates. For example, the control unit can adjust initial rates, of the administration of the composition including an effective amount of an oxygen antagonist into the organism, to levels that enable the organism to reduce transpiration and thus minimize water consumption. The control unit can coordinate the components (i)-(v) necessary to monitor a single organism. Alternatively, the control unit can coordinate numerous components (i)-(v) that are necessary to monitor many organisms throughout a geographical area. Also, one or more user interfaces, such as those commonly used in the art, can be included anywhere within the apparatus. Each user interface optionally includes a display, such as a touch screen display, and various manual inputs.

The Communications Interface (v): The communications interface facilitates the exchange of information between components (i)-(v) and may consist of wiring, (e.g., via hard wiring, a serial port, a USB port, a "fire wire" port, etc.), or wireless connections (e.g., connected an via infrared connection, a radio frequency connection, a "bluetooth" connection, etc.).

Receptacles: The apparatus may further include a receptacle or container for storing a supply of the composition including an effective amount of an oxygen antagonist. Additional receptacles can optionally be used to store one or more additives that modulate growth of the organism (e.g., antivirals or any agent to accelerate or retard root growth). Alternatively, such additives can be combined in a single receptacle with the composition including an effective amount of an oxygen antagonist. The receptacle can be of any size or shape and consist of any material such as plastic, metal, or glass.

In some embodiments, the above-described apparatus is automated to control the rates at which the composition including an effective amount of an oxygen antagonist is provided (e.g., injected or sprayed) to one or more organisms. In some embodiments, the rate of injection or spraying is substantially constant over the period of time. In some embodiments, injection or spraying is conducted under pressure. In this regard, the pressure may be in excess of one pound per square inch (psi, 0.007 MPa), such as from about 1 psi to about 100 psi (0.7 MPa), or from about 100 psi to about 1000 psi (7 MPa), or a range between and including any two of these values.

In some embodiments, the oxygen antagonist comprises hydrogen sulfide, a prodrug or salt thereof. In other embodiments, the apparatus is for modulating transpiration in multiple organisms. In some embodiments, the communications interface is adapted for wireless communication. In other embodiments, the apparatus further includes a receptacle (e.g., container) for storing the composition.

According to another exemplary embodiment, the present technology provides method for modulating transpiration in an organism that is capable of photosynthesis, including: contacting the organism with an initial concentration of a composition including an effective amount of an oxygen antagonist; measuring at least one parameter; and increasing or decreasing the initial concentration of the composition that is contacted with the organism: where the parameter is selected from the group consisting of: the amount of light that irradiates the organism; the temperature of the organism; the amount of $CO_2$ that is absorbed by the organism; the amount of moisture that is present in the soil surrounding the roots of the organism; and the concentration of the composition within the organism. In some embodiments, the oxygen antagonist includes hydrogen sulfide, a prodrug or salt thereof.

In some embodiments, the method further includes determining an optimum concentration at which the composition should be contacted with an organism, where the optimum concentration is based on a goal selected from the group consisting of: maximizing the yield of a crop that is produced by the organism; minimizing the amount of water that is transpired by the organism; minimizing the amount of water that is provided to the organism; minimizing the amount of fertilizer that is provided to the organism; and minimizing the cost of growing the organism.

The present technology, thus generally described, will be understood more readily by reference to the following Examples, which are provided by way of illustration and is not intended to be limiting of the present technology.

EXAMPLES

Example 1

Stomata Conductance and Transpiration in Greenhouse-Grown Plants

In the following example, a treatment group of dwarf sunflower (*Helianthus annuus* L.) plants is sprayed once each evening with an aqueous "treatment solution" of 10 ppm sodium hydrosulfide (NaHS) in distilled water, buffered with phosphate, to a pH of 7.4. The control group of plants is sprayed once each evening with an equivalent amount of "control solution" consisting of distilled water buffered with phosphate to a pH of 7.4. The treatment and control groups each include seven plants. The dwarf sunflower plants are grown from seed in 20-cm diameter plastic pots. Each pot contains one plant growing in a peat, sand mixture. The plants are grown in a greenhouse with a 15 h light period and a radiation flux of 450 to 550/anol/m2 provided by lamps. Daytime and nighttime temperatures are about 26° C. and 16° C. respectively. Relative humidity ranges between about 30% to 40%. Plants are watered to field capacity daily.

Approximately 60 ml of treatment solution is sprayed onto the top surface and bottom surface of leaves of seven plants in the treatment group using a simple hand sprayer. The control group receives approximately 60 ml of control solution, sprayed onto the leaves in the same fashion as the treated plants. Both the treated group and the control group are sprayed once per evening after sunset for one week.

Stomata conductance is measured with a steady state porometer (LiCor model LI-1600, LiCor Inc., Lincoln, Nebr.). Measurements are made on the abaxial leaf surfaces where the majority of stomata are located and are recorded after the treated group and the control group are sprayed once per evening for one week.

The transpiration rate is determined by calculating the vapor pressure at the evaporating surface (leaf) and the air vapor pressure. The saturated vapor pressure of the leaf is calculated by measuring leaf temperature. Leaf temperature is measured using an external thermocouple as well as the LICor porometer. The air vapor pressure is determined from the relative humidity and air temperature according to the following equation: $e_a = e_s * hr$ where $e_s$ is the saturated vapor pressure at the air temperature, $e_a$ is the actual vapor pressure and hr is the relative humidity. The saturated vapor pressure can be obtained from tables or diagrams which relate vapor pressure to temperature and relative humidity. Relative humidity is determined using a sling psychrometer. Transpiration rates are determined from the stomata conductance and vapor pressures according to the following equation:

$$E = g_v(e_s - e_a/pa)$$

where E=transpiration rate, $e_s$ is the vapor pressure at the saturated surface (leaf), $e_a$ is the air vapor pressure and pa is the atmospheric pressure. Stomata conductance and transpiration are calculated for a single leaf without extrapolating to the entire plant. Averages for 7 plants of each group are calculated and plotted.

It is contemplated that foliar application of aqueous sodium hydrosulfide (NaHS) on sunflower plants may induce a decrease in stomata conductance in plants treated at night compared to control plants similarly treated at night. A decrease in transpiration can be explained by a reduction in stomata conductance (closure of stomata to reduce water loss).

Example 2

Transpiration Reduction in Pepper Plants Grown in a Growth Chamber

In the following example, a treatment group of potted pepper (*Capsicum* sp.) plants is sprayed once each evening with an aqueous "treatment solution" of 10 ppm sodium hydrosulfide (NaHS) in distilled water, buffered with phosphate, to a pH of 7.4. The control group of plants is sprayed once each evening with an equivalent amount of "control solution" consisting of distilled water buffered with phosphate to a pH of 7.4. Potted pepper plants are grown in a temperature controlled growth-chamber under metal halide lamps. Average temperature in the growth chamber is about 20° C., and relative humidity is about 60%. Pots contain a greenhouse mix peat soil enriched with slow release fertilizer. Environmental conditions (light, temperature, and relative humidity) inside the growth chamber are monitored every 30 minutes during the experiment using standard environmental sensors such as a pyranometer, thermocouple psychrometer, relative humidity sensor and a datalogger. A set of 24 pepper plants are used to evaluate the application of aqueous sodium hydrosulfide (NaHS) on drought resistance and transpiration. Two groups of 6 plants per group are watered to keep the water content near field capacity (optimally watered groups). Each of the 6 plants in one of these optimally watered groups receives a treatment solution of aqueous sodium hydrosulfide (NaHS) application as described. The other 6 plants in the optimally watered group receive the control solution of just water. Two other two groups of 6 plants per group are only watered when the soil reaches the permanent wilting water potential (which corresponds to about two to three days without watering). These two groups are designated water stressed groups. Each of the 6 plants in one of the water stressed groups receives the treatment solution of aqueous sodium hydrosulfide (NaHS) as described. The other 6 plants in the water stressed group receive the control solution of just water.

The treatment solution of aqueous sodium hydrosulfide (NaHS) is sprayed once each night onto the top surface and bottom surface of leaves as described in Example 1 using a simple hand sprayer. The control group receives the same quantity of water alone which is sprayed each night onto the leaves in the same fashion as the treated group. As noted, both the treated group and the control group are sprayed once per evening after sunset.

Daily transpiration rates are monitored by weighing the pots each day to record the corresponding water use and then refilling the water to field capacity. It is contemplated that the plants that are optimally watered and spayed with treatment solution of aqueous sodium hydrosulfide (NaHS) may exhibit a reduction in transpiration compared to control plants.

It is further contemplated that, under water stress conditions, the cumulative water use in control plants is consistently higher than that in the plants spayed with treatment solution of aqueous sodium hydrosulfide (NaHS). Any reduction in the use of water by NaHS-treated plants under water stress (drought) conditions is likely a direct result of reduced stomata conductance that may be induced by hydrogen sulfide.

Example 3

Reducing the Water Used to Irrigate Corn Grown Under Field Conditions

Under both greenhouse and controlled growth chamber experiments, it is contemplated that hydrogen sulfide will demonstrate a significant effect in reducing stomata conductance and transpiration. These expectations may be further tested under field conditions.

In the following example, a treatment group of corn (*Zea Maize*) is sprayed once each evening with an aqueous "treatment solution" of 10 ppm sodium hydrosulfide (NaHS) in distilled water, buffered with phosphate, to a pH of 7.4. The control group of plants is sprayed once each evening with an equivalent amount of "control solution" consisting of distilled water buffered with phosphate to a pH of 7.4. An experimental plot may be setup with 8 repetitions to obtain statistically independent results. The treatment (aqueous NaHS) and control (water alone) plots may be set up following a randomized scheme. The plots may be tilled to a depth of approximately 30 cm and a chemical fertilizer (16% N, 16% P, 16% K) may be applied by incorporation into the soil during tillage.

Water Use Measurements. It is contemplated that the total water used by corn crops in the control group will exceed the total for corn crops treated with NaHS. To measure water use of the corn, a dripping irrigation system may be used such that water is supplied to the plots when a threshold value of soil water content is reached. This allows the measurement of water used in every single plot such that evaluation of water use differences between the water-alone control crops and NaHS treated crops can be monitored. The system is installed in such a way that every plant may receive a given amount of water determined by using constant rate water applicators. The applicators may, for example, apply water at a constant rate 2 gal/hr (7.56 liters/hour). Irrigation pipes may be activated by electrical valves. Soil water content (SWC) is measured continuously, using a Time Domain Reflectometer sensor installed in each of the twenty-four rows. Twenty-four transmission line oscillator (TLO) probes (model CS615-L water content reflectometer, Campbell Scientific Inc. Logan, Utah) are installed in the field. The sensors are monitored by a datalogger (model 23X, Campbell Scientific Inc., Logan, Utah). The probes may be 30 cm long, and can be buried vertically, such that average volumetric water content of the top 30 cm of the soil is measured. The probes may be installed in the middle of the plant rows. The soil water content may be measured every 60 seconds. Averages of the reading may be output every 60 minutes and stored in the datalogger. The TLO may be calibrated against gravimetric water contents and latter are converted to volumetric water content by using the bulk density.

At midnight, SWC is measured. If, for every specified row, SWC is below 25% in volume, the irrigation system may be activated to irrigate for the total time required to replenish the specified soil volume to Field Capacity (FC). Every plant is irrigated by one drip irrigator, having a steady irrigation rate of 2 gal/hr. The total amount of water applied per row is obtained by multiplying the minutes of irrigation per day by the irrigation rate by the number of drip irrigators, while the total amount of water per plant is obtained by considering only one drip irrigator. The application rate may be set in such a way that the irrigation rate is always less than the infiltration rate in order to avoid the formation of ponds or the occurrence of runoff. The datalogger (controlling the irrigation system) may be programmed in the following way: the water content may be read by the TLO probes, the data for every row may be compared to the threshold value (Field Capacity). If the values are below FC, the irrigation may start and run until the soil water content is replenished to FC. In this way, the soil is kept at a constant water content approximately corresponding to FC. FC value may be calculated from an empirical equation that accounts for soil textural data. Two parameters obtained from soil textural data are slope of the water retention curve and air entry potential. The equations to be used are those as described in *Soil Physics With Basic* by Gaylon S. Campbell, published by Elsevier Science Publishing (1985). Values of the above parameters are used to obtain values of soil water content at the corresponding soil water potential of $-33$ J/Kg (defined Field Capacity). Soil particle size analysis may be performed in order to obtain the mentioned parameters.

Weather Data. Weather data may be collected including daily rainfall, daily average air temperature, daily global solar radiation and daily average wind speed. Hourly rainfall is summed to obtain the cumulative value over a day, air temperature is averaged and max and min temperatures are recorded, global solar radiation is summed to obtain cumulative daily data, wind speed is averaged, relative humidity is used together with air temperature to calculate the vapor pressure deficit that is then averaged.

Biomass Determination. Total Dry Biomass (TDB) may be measured for the entire plant and for different sections (such as stems, leaves and yield) at the end of the growing season. Dry weight determinations are made after drying plants at 60° C. for three days. It is contemplated that the total water used by crops in the control group will exceed the total for crops treated with NaHS.

Biomass Production and Water Use Efficiency. Water Use Efficiency (WUE) is defined as the ratio between the total yield and the total plant water use (TWU), WUE=TDM/TWU. This index gives an important indication on the ability of the crop to utilize water to produce yield. It is contemplated that the Water Use Efficiency (WUE) by corn crops in the control group will be less than that for corn crops treated with NaHS.

For example, the total dry matter (TDM) can be determined for corn crops in the control group will exceed the total for corn crops treated with NaHS. It is contemplated that the treated corn crops will show a higher biomass production compared to non-treated control corn. The relative difference may be 10%, 20%, 30%, 40%, 50%, 60%, 70%, 80%, 90%, or a range between any two of those values.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A method for modulating transpiration in an organism that is capable of photosynthesis, wherein the method comprises contacting the organism with a composition comprising an effective amount of an oxygen antagonist, wherein the oxygen antagonist comprises a hydrogen sulfide prodrug or salt thereof, wherein the prodrug is a hydrogen sulfide releasing polymer of Formula II:

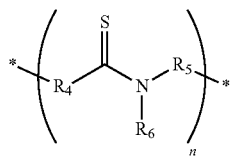

wherein
$R_4$ is selected from amino, alkylene, heteroalkylene, arylene, and heteroarylene;
$R_5$ is selected from alkylene, and arylene;
$R_6$ is selected from hydrogen, alkyl, and aryl; and
n is from 1 to 1,000.

2. The method of claim 1, wherein the hydrogen sulfide releasing polymer is co-polymerized with a polycarbonate, polyolefin, polyamide, polyester, polyacrylate, or a mixture thereof.

3. The method of claim 1, wherein the composition is a gas, liquid, gel, topical spray, coating, or a suspension.

4. The method of claim 1, wherein the composition further comprises an excipient.

5. The method of claim 4, wherein the excipient is selected from a fungicide, antibiotic, antiviral, pesticide, growth regulator, nutrient, fertilizer, filler, surfactant, wetting agent, inert additive, or a combination thereof.

6. The method of claim 1, wherein the contacting step is dependent upon the amount of light that irradiates the organism.

7. The method of claim 1, wherein the contacting occurs between sunset and sunrise and does not occur between sunrise and sunset.

8. The method of claim 1, wherein the contacting step is dependent upon the time of day.

9. The method of claim 7, wherein sunrise and/or sunset comprise an artificially induced light-dark cycle.

10. The method of claim 9, wherein the artificially induced light-dark cycle comprises artificial light, artificially induced darkness, shading, or a combination thereof.

11. The method of claim 1, wherein the composition inhibits light-independent (i.e., "dark") photosynthetic reactions within the organism.

12. The method of claim 1, wherein the composition reduces stomatal conductivity.

13. The method of claim 1, wherein the contacting step is dependent upon the temperature of the organism.

14. The method of claim 1, wherein the contacting step occurs above a threshold temperature.

15. The method of claim 14, wherein the threshold temperature is about 30° C.

16. The method of claim 1, wherein the contacting step is dependent upon the amount of $CO_2$ that is absorbed by the organism.

17. The method of claim 1, further comprising reducing the rate of absorption of atmospheric $CO_2$ by the organism.

18. The method of claim 1, wherein the contacting step is dependent upon the amount of moisture that is present in the soil surrounding the roots of the organism.

19. The method of claim 1, further comprising measuring the amount of moisture that is present in the soil surrounding the roots of the organism.

20. The method of claim 1, wherein the contacting step comprises adding the composition to the atmosphere that contacts the organism.

21. The method of claim 1, wherein the contacting step comprises coating at least a portion of the organism with the oxygen antagonist.

22. The method of claim 1, wherein the contacting step comprises providing the oxygen antagonist to the roots of an organism, wherein the organism is a plant.

23. The method of claim 22, wherein the contacting step comprises providing the oxygen antagonist to the roots of the plant via drip irrigation.

24. The method of claim 1, wherein the method further comprises adjusting the amount of the composition that is provided to the organism.

25. The method of claim 1, wherein the organism is grown in a controlled environment.

26. The method of claim 25, wherein the controlled environment is a greenhouse, grow-house, or grow room.

27. The method of claim 1, wherein the organism comprises algae.

28. The method of claim 27, wherein the algae produces a feedstuff or feedstock.

29. The method of claim 1, wherein the organism is a plant.

30. The method of claim 29, wherein the plant is grown on a farm, orchard, or in a forest.

31. The method of claim 29, wherein the plant produces a grain, fruit, vegetable, feedstuff, or feedstock.

32. The method of claim 29, wherein the plant produces soybean, corn, wheat, barley, oats, rye, rape, millet, rice, sunflower, cotton, sugar beets, bananas, strawberries, blueberries, almonds, grapes, mango, papaya, peanuts, potatoes, tomatoes, peppers, cucurbits, cucumbers, melons, watermelons, garlic, onions, carrots, cabbage, beans, peas, lentils, alfalfa, trefoil, clovers, flax, herb, grass, lettuce, sugar cane, tea, tobacco, coffee, or adornment.

33. The method of claim 29, wherein the plant is a tree.

34. The method of claim 33, wherein the composition is provided into the vasculature system of the tree or to the immediate proximity thereof.

35. The method of claim 1, wherein the method is at least partially automated.

36. A method for modulating transpiration in an organism that is capable of photosynthesis, comprising:

contacting the organism with an initial concentration of a composition comprising an effective amount of an oxygen antagonist, wherein the oxygen antagonist comprises a hydrogen sulfide prodrug or salt thereof, wherein the prodrug is a hydrogen sulfide releasing polymer of Formula II:

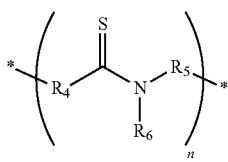

wherein $R_4$ is selected from amino, alkylene, heteroalkylene, arylene, and heteroarylene;

$R_5$ is selected from alkylene, and arylene;

$R_6$ is selected from hydrogen, alkyl, and aryl; and n is from 1 to 1,000;

measuring at least one parameter; and increasing or decreasing the initial concentration of the composition that is contacted with the organism;

wherein the parameter is selected from the group consisting of:

the amount of light that irradiates the organism;

the temperature of the organism;

the amount of $CO_2$ that is absorbed by the organism;

the amount of moisture that is present in the soil surrounding the roots of the organism; and the concentration of the composition within the organism.

37. The method of claim 36, further comprising determining an optimum concentration at which the composition should be contacted with the organism, wherein the optimum concentration is based on a goal selected from the group consisting of:

maximizing the yield of a crop that is produced by the organism;

minimizing the amount of water that is provided to the organism;

minimizing the amount of water that is transpired by the organism;

minimizing the amount of fertilizer that is provided to the organism; and minimizing the cost of growing the organism.

* * * * *